United States Patent [19]

Yukawa et al.

[11] Patent Number: 4,772,376
[45] Date of Patent: Sep. 20, 1988

[54] AIR/FUEL RATIO SENSOR HAVING OXYGEN SENSOR CELL AND OXYGEN PUMP CELL

[75] Inventors: Fumio Yukawa; Masayuki Touda; Shinji Kimura; Fumio Munakata; Satoru Ichikawa, all of Yokosuka, Japan

[73] Assignee: Nissan Motor Co., Ltd., Yokohama, Japan

[21] Appl. No.: 23,809

[22] Filed: Mar. 9, 1987

[30] Foreign Application Priority Data

Mar. 11, 1986 [JP] Japan .................................. 61-54405
Sep. 3, 1986 [JP] Japan .................................. 61-205805

[51] Int. Cl.$^4$ .............................................. G01N 27/58
[52] U.S. Cl. ........................................ 204/410; 204/412; 204/425; 338/34
[58] Field of Search ............... 204/410, 412, 425, 426, 204/1 S; 338/34

[56] References Cited

U.S. PATENT DOCUMENTS 4,579,643 4/1986 Mase et al. ......................... 204/427

FOREIGN PATENT DOCUMENTS 60-236056 11/1985 Japan .................................. 204/425
61-30758 2/1986 Japan .................................. 204/425

Primary Examiner—G. L. Kaplan
Attorney, Agent, or Firm—Foley & Lardner, Schwartz, Jeffery, Schwaab, Mack, Blumenthal & Evans

[57] ABSTRACT

An air/fuel ratio sensor has an oxygen sensor cell including a primary measuring element in direct contact with a gas such as exhaust gases of an automotive engine, and an oxygen pump cell formed by inner and outer electrodes and a cover of an oxygen ion conductive solid electrolyte which confines the primary measuring element within a gas diffusion control space, and which has a small gas diffusion hole. The primary measuring element is formed with a central opening whose center lies right below the gas diffusion hole, in order to reduce a burden imposed on the oxygen pump cell and prevent overshoot in a sensor response characteristic. The oxygen sensor cell may be composed of the primary measuring element of a transition metal oxide connected with a pair of electrodes for measurement of an electrical resistance of the primary element, or may be composed of an oxygen ion conductive solid electrolyte substrate sandwiched between a reference electrode and the primary measuring element which serves as a measuring electrode.

16 Claims, 14 Drawing Sheets

AIR/FUEL RATIO SENSOR HAVING OXYGEN SENSOR CELL AND OXYGEN PUMP CELL

BACKGROUND OF THE INVENTION

The present invention relates to air/fuel ratio sensors used for internal combustion engines or other combustion engines, and more specifically to air/fuel ratio sensors of a type having an oxygen sensor cell and an oxygen pump cell.

Japanese patent provisional publication No. 60-236056 discloses one conventional example of such air/fuel ratio sensors. As shown in FIG. 7, the oxygen sensor cell of this example has a primary element of metal oxide, such as a transition metal oxide, whose electrical resistance changes with change in oxygen concentration. The oxygen pump cell has a member of oxygen ion conductive solid electrolyte.

Japanese patent provisional publication No. 61-30758 discloses another conventional example which is shown in FIG. 20A. The oxygen sensor cell of this example is composed of a substrate of oxygen ion conductive solid electrolyte, which is sandwiched between a reference electrode in direct contact with a reference gas such as air, and a measuring electrode in direct contact with a gas to be measured.

However, these air/fuel ratio sensors are unsatisfactory in that the burden of the oxygen pump cell is too much, and the tendency to overshoot in a transient response is too high, as explained hereinafter more in detail.

SUMMARY OF THE INVENTION

It is an object of the present invention to provide an air/fuel ratio sensing device which is superior in the durability of the pump cell and the transient response characteristic.

According to the present invention, a device for sensing an air/fuel ratio comprises sensing means and controlling means. The sensing means comprises a substrate and a primary measuring element mounted on a first surface of the substrate. The controlling means comprises a first cover mounted on the substrate for enclosing the primary element within a control space formed between the substrate and the first cover. The first cover is formed with at least one hole for allowing a gas to move into and out of the control space. At least a part of the cover is made of an oxygen ion conductive solid electrolyte. The controlling means further comprises inner and outer electrodes forming an oxygen pump cell with the oxygen ion conductive solid electrolyte. The inner electrode is attached to an inner surface of the first cover within the control space. The outer electrode is attached to an outer surface of the first cover outside the control space. The primary element of the present invention is disposed outside a projection of the hole formed by projecting the hole onto the first surface of the substrate along a line along which the hole extends.

The primary element is mounted on the substrate and exposed to the gas in the control space. In some embodiments of the present invention, the primary element is made of a metal oxide whose electrical resistance changes in dependence on an oxygen concentration of a gas to be measured. In the other embodiments, the primary element is a measuring electrode mounted on the substrate of an oxygen conductive solid electrolyte.

In the illustrated embodiments of the present invention, the first surface of the substrate is substantially flat, the hole extends through the first cover along a line substantially perpendicular to the upper surface of the substrate, and the primary element has an opening whose center is situated just below the hole and whose size is larger than that of a cross section of the hole. A boundary surface of the hole and the above-mentioned projection are geometrically related so that the boundary surface of the hole is a surface generated by moving a straight line perpendicular to the first surface of the substrate, and during this motion, the straight line intersects the first surface of the substrate always at a point lying on an outline of the projection.

DETAILED DESCRIPTION OF THE INVENTION

To facilitate understanding of first and second embodiments of the present invention, reference is first made to a conventional air/fuel ratio sensor as disclosed in Japanese provisional publication No. 60-236056.

Figure 7:
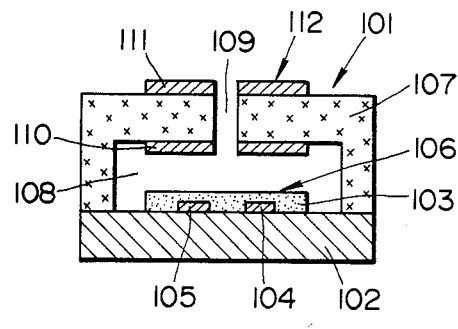
FIG. 7 is a sectional view of a conventional air/fuel ratio sensor of the same type as the sensors of the first and second embodiments.

A primary measuring element 103 of an air/fuel ratio sensor 101 shown in FIG. 7 is made of metal oxide, such as an oxide of a transition metal, whose electrical resistance varies in accordance with change in oxygen concentration of a gas to be measured. The metal oxide primary element 103 is formed in the shape of a layer on an upper surface of a flat substrate 102 of insulating material. First and second electrodes 104 and 105 are attached to the metal oxide primary element 103 to measure the electrical resistance of the primary element 103. An oxygen sensor cell 106 composed of the primary element 103 and the first and second electrodes 104 and 105 is enclosed by a cover 107 of an oxygen ion conductive solid electrolyte, within a gas diffusion control space 108 formed between the cover 107 and the oxygen sensor cell 106. The solid electrolyte cover 107 is formed with a small gas diffusion hole 109. Annular third and fourth electrodes 110 and 111 are attached, respectively, to inner and outer surfaces of the solid electrolyte cover 107 around the hole 109 to form an oxygen pump cell 112.

Figure 8:
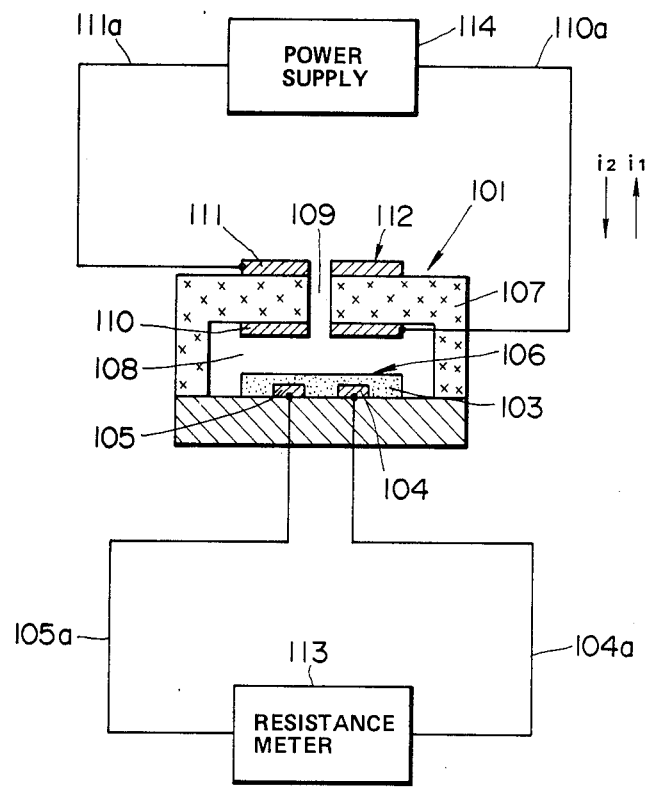
FIG. 8 is a circuit diagram showing a circuit for detecting the air/fuel ratio by using the sensor of FIG. 7.

In a circuit shown in FIG. 8, the air/fuel ratio sensor 101 of FIG. 7 is connected with a resistance meter 113 and a power supply 114 for the pump cell 112. The resistance meter 113 is connected between the first and second electrodes 104 and 105 of the oxygen sensor cell 106 through leads 104a and 105a. The power supply 114 is connected between the third and fourth electrodes 110 and 111 of the pump cell 112 through leads 110a and 111a.

Figure 9:
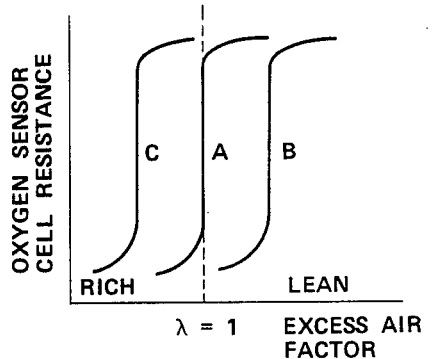
FIG. 9 is a graph showing resistance versus excess air factor relationships of the air/fuel ratio sensor of FIG. 7.

When no pump current is supplied from the power supply 114, the resistance of the metal oxide element 103 measured by the resistance meter 113 varies in dependence on the oxygen concentration of the gas flowing into the control space 108 through the hole 109 according to a characteristic A shown in FIG. 9, which has a large and sharp change of the resistance at or near the A/F equivalent ratio (excess air factor) "lambda"=1.

When a pump current in a direction $i_1$ shown in FIG. 8 is supplied from the power supply 114, oxygen ions flow through the solid electrolyte cover 107 from the third inner electrode 110 to the fourth outer electrode 111, so that oxygen is consumed near the third inner electrode 110. In the case that the movement of the gas in the gas diffusion control space 108 and/or the gas diffusion hole 109 is a rate-determining step, the oxygen concentration becomes low near the metal oxide element 103 especially in a region remote from the gas diffusion hole 109 even if the ambient gas contains a high percentage of oxygen (that is, the ambient gas is lean.). Therefore, the air fuel ratio sensor 101 provides a characteristic B shown in FIG. 9, so that the air/fuel ratio control becomes possible on the lean side.

When the pump current in a direction $i_2$ shown in FIG. 8 is supplied from the power supply 114, oxygen ions flow in the solid electrolyte cover 107 from the fourth outer electrode 111 to the third inner electrode 110, so that oxygen is supplied into the control space 108 near the third electrode 110. Therefore, even if the ambient gas contains only a low percentage of oxygen (that is, the gas is rich.), the oxygen concentration becomes high near the metal oxide element 103 especially in the region remote from the gas diffusion hole 109. In this case, a characteristic C of FIG. 9 is obtained, and the air/fuel ratio sensor 101 enables the air/fuel ratio control on the rich side.

Figure 10:
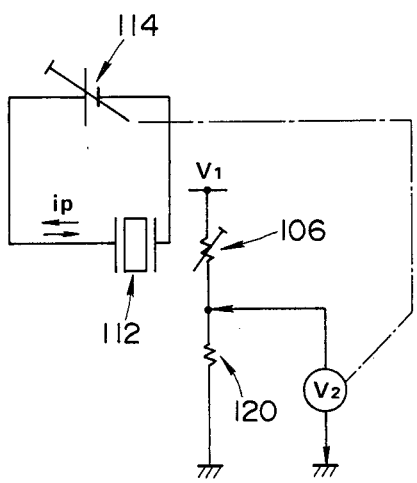
FIG. 10 is a diagram of an equivalent circuit arranged to measure the excess air factor (air/fuel equivalent ratio) by using the sensor of FIG. 7.
Figure 11:
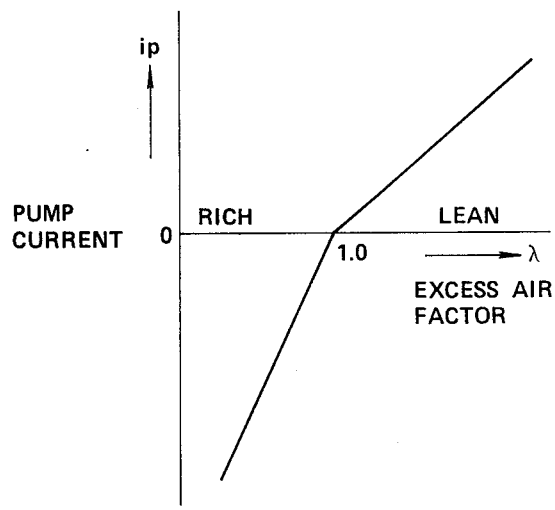
FIG. 11 is a graph showing a pump current versus excess air factor relationship of the equivalent circuit of FIG. 10.

An equivalent circuit shown in FIG. 10 is one example used in actual systems for measuring the excess air factor of exhaust gases. In the circuit of FIG. 10, the oxygen sensor cell 106 and a resistor 120 are connected in series to form a series combination, to which a constant voltage $V_1$ is applied. The resistance of the metal oxide element 103 of the oxygen sensor cell 106 is measured from an output voltage $V_2$ obtained from an intermediate tap between the sensor cell 106 and the resistor 120. The power supply 114 is arranged to supply the pump current ip so as to maintain the output voltage $V_2$ at a predetermined value Va. Therefore, the pump current ip varies in dependence on the excess air factor "lambda" of the gas, as shown by a characteristic of FIG. 11.

Figure 12A:
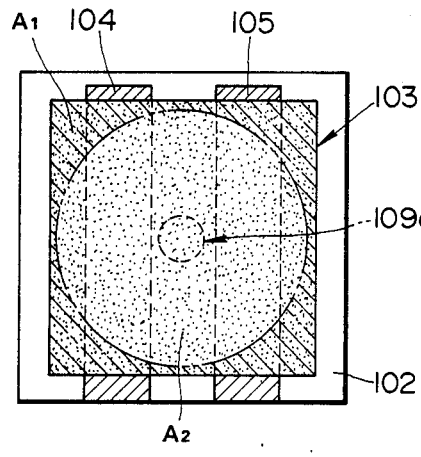
FIG. 12A is a plan view of the sensor of FIG. 7 for showing a low resistivity region ($A_1$) of the metal oxide element in a lean atmosphere.
Figure 12B:
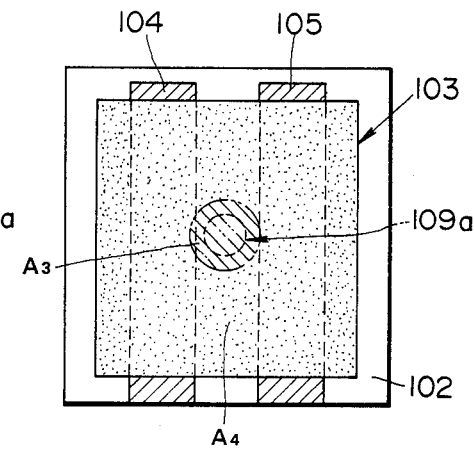
FIG. 12B is a plan view of the sensor of FIG. 7 for showing a low registivity region ($A_3$) of the metal oxide element in a rich atmosphere.
Figure 13:
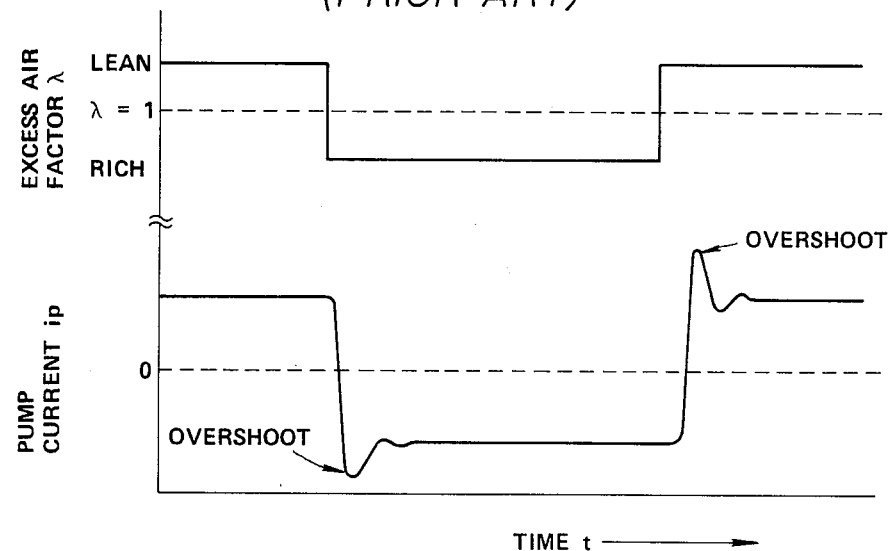
FIG. 13 is a graph showing an output characteristic of the sensor of FIG. 7.

However, the conventional air/fuel ratio sensor 101 is still unsatisfactory in the following points. FIG. 12A schematically shows the metal oxide element 103 in the case that the gas to be measured is lean. As shown by a two-dot chain line in FIG. 12A, the metal oxide element 103 is held at a low resistivity state in a region $A_1$ remote from a projection 109a of the gas diffusion hole 109. When the gas is rich, the metal oxide element 103 is held at the low resistivity state only in a region $A_3$ closest to the projection 109a, and the remaining region $A_4$ of the element 103 is held at a high resistivity state. Therefore, in order to maintain the output voltage $V_2$ at the predetermined value Va, it is necessary to maintain the oxygen concentration sufficiently high in most of the gas diffusion control space 108 by supplying excessive pump current more on the rich side, as compared with on the lean side. This promotes degradation of the oxygen pump cell performance. Furthermore, overshoots tend to occur in a transient response of the pump current ip resulting from changes of the gas from rich to lean and from lean to rich, as shown in FIG. 13, because too much pump current is required to remove an excess of oxygen in the diffusion control space 108 especially on the rich side.

Figure 1A:
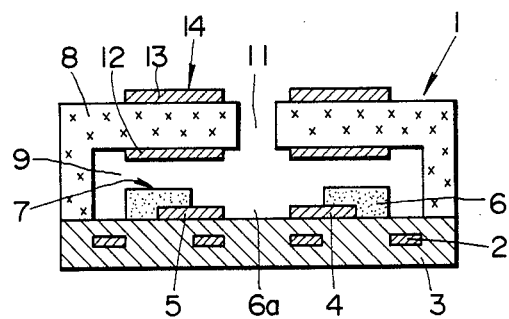
FIG. 1A is a sectional view, taken on a line I-1 of FIG. 1B, schematically showing an air/fuel ratio sensor of a first embodiment of the present invention.
Figure 1B:
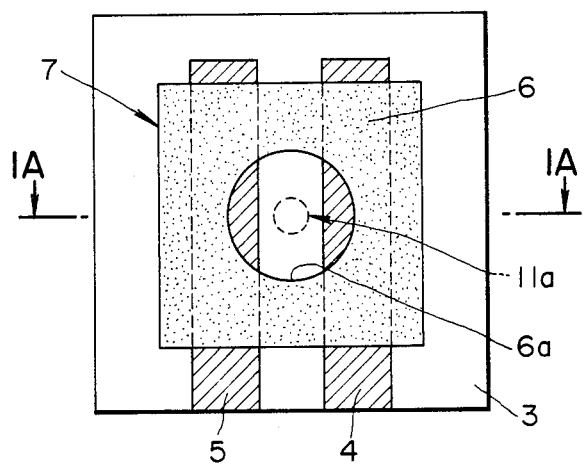
FIG. 1B is a plan view of the air/fuel ratio sensor of FIG. 1A whose cover is removed to show its interior construction.

A first embodiment of the present invention is shown in FIGS. 1A and 1B. An air/fuel ratio sensor 1 of FIGS. 1A and 1B has an insulating substrate 3 in the shape of a flat plate. The insulating substrate 3 of an insulating material has a heating element 2 embedded therein. A first electrode 4 and a second electrode 5 are mounted on an upper surface of the substrate 3. The upper surface of the substrate 3 of this embodiment is substantially flat. Each of the first and second electrodes 4 and 5 of this embodiment is shaped like a strip, and placed in parallel to the other on the upper surface of the substrate 3. An oxygen sensing primary element 6 is placed on the first and second electrodes 4 and 5. The sensing element 6 is made of a metal oxide such as an oxide of a transition metal (or an oxide of a non-transition metal such as Sn or Zn). The sensing metal oxide element 6 is thin and substantiallty flat, and has a circular opening 6a, which is located in a central part of the metal oxide element 6. In this embodiment, the metal oxide element 6 is substantially square, and the center of the opening 6a coincides with the center of the square metal oxide element 6. An oxygen sensor cell 7 is constituted by the first and second electrodes 4 and 5 and the metal oxide element 6. The first and second electrodes 4 and 5 are attached to the metal oxide element 6 to measure change in the electrical resistance of the metal oxide element 6.

A cover 8 is placed on the substrate 3 so as to cover the oxygen sensor cell 7, and to form a gas diffusion control space 9 between the substrate 3 and the cover 8. The oxygen sensor cell 7 is enclosed within the control space 9 by the cover 8. The cover 8 is made of an oxygen ion conductive solid electrolyte. The cover 8 is formed with a gas diffusion hole 11 located at a center of the cover 8. A gas of an ambient atmosphere can flow into and out of the gas diffusion control space 9 through the gas diffusion hole 11. The cover 8 has a flat top wall and a side wall extending from a periphery of the top wall to the substrate 3. The flat top wall of the cover 8 of this embodiment is substantially square, and substantially parallel to the substrate 3. The gas diffusion hole 11 is located at the center of the top wall of the cover 8. The hole 11 of this embodiment is circular, and extends through the top wall of the cover 8 in a direction substantially perpendicular to the top surface of the substrate 3. A circular projection 11a shown in FIG. 1B is produced by projecting the hole 11 of the cover 8 onto the top surface of the substrate 3 in the direction in which the hole 11 extends through the top wall of the cover 8. As shown in FIG. 1B, the projection 11a of the hole 11 is concentric with the circular opening 6a of the oxygen sensing metal oxide element 6. The diameter of the circular opening 6a is larger than that of the projection 11a. That is, the projection 11a is centered within the circular opening 6a. In this way, the oxygen sensing element 6 is placed outside the projection 11a.

The air/fuel ratio sensor 1 further has a third inner electrode 12 and a fourth outer electrode 13 which form an oxygen pump cell 14 together with the solid electrolyte of the cover 8. Each of the third and fourth electrodes 12 and 13 is shaped like a ring, and disposed around the gas diffusion hole 11. The third electrode 12 is attached to an inner surface of the cover 8 within the gas diffusion control space 9, and the fourth electrode 13 is attached to an outer surface of the cover 8 outside the control space 9.

Figure 2:
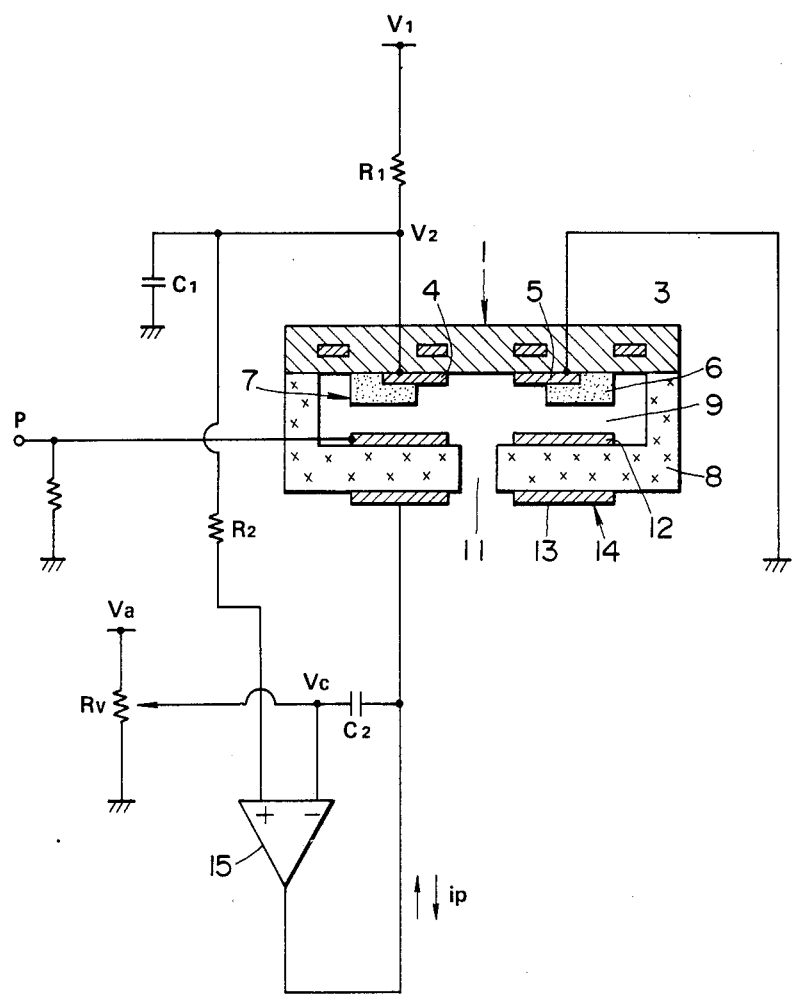
FIG. 2 is a diagram of a circuit including the air/fuel sensor of FIG. 1A, arranged to detect the air/fuel ratio.

FIG. 2 shows an example of an air/fuel ratio control circuit using the air/fuel ratio sensor 1 of this embodiment. The circuit of FIG. 2 is arranged to determine the air/fuel ratio from an oxygen pump current of the air/fuel ratio sensor 1.

The circuit of FIG. 2 includes a differential amplifier 15. A first input (minus side) of the differential amplifier 15 is held at a reference voltage Vc. A resistor $R_1$ and the metal oxide element 6 are connected in series to form a voltage divider, to which a constant voltage $V_1$ is applied. An output voltage $V_2$ obtained from an intermediate tap between the resitor $R_1$ and the element 6 is applied to a second input terminal (plus side) of the differential amplifier 15. The differential amplifier 15 supplies the pump current ip to the oxygen pump cell 14 so as to make the output voltage $V_2$ equal to the reference voltage $V_c$.

Figure 3:
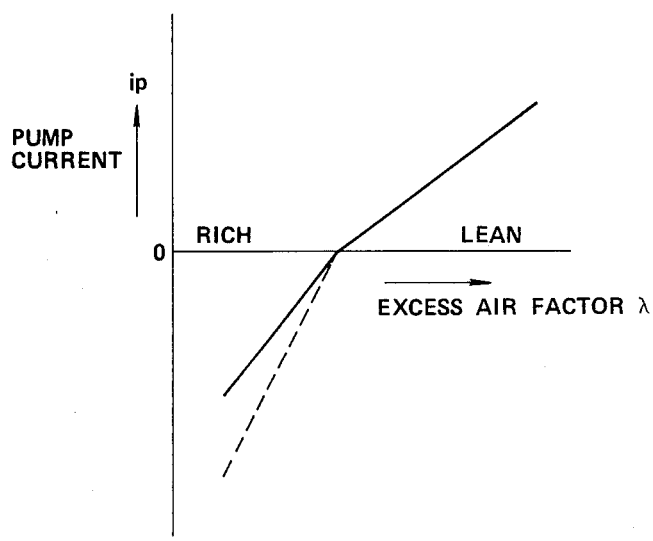
FIG. 3 is a graph of a characteristic of a pump current ip of the circuit of FIG. 2 versus an excess air factor "lambda" of the gas being measured.

This air/fuel ratio sensor 1 has a characteristic between the pump current ip and the excess air factor "lambda" of the gas to be measured, shown by a solid line in FIG. 3. A broken line in FIG. 3 shows a characteristic of the conventional air/fuel ratio sensor 101 shown in FIG. 7. As shown in FIG. 3, the value of the pump current of the sensor 1 is lower than that of the conventional sensor 101 especially on the rich side. Therefore, the design of the air/fuel ratio sensor 1 of the present invention can reduce the burden of the oxygen pump cell 14, and limit the undesired aging of the output characteristic to a low level.

Figure 4:
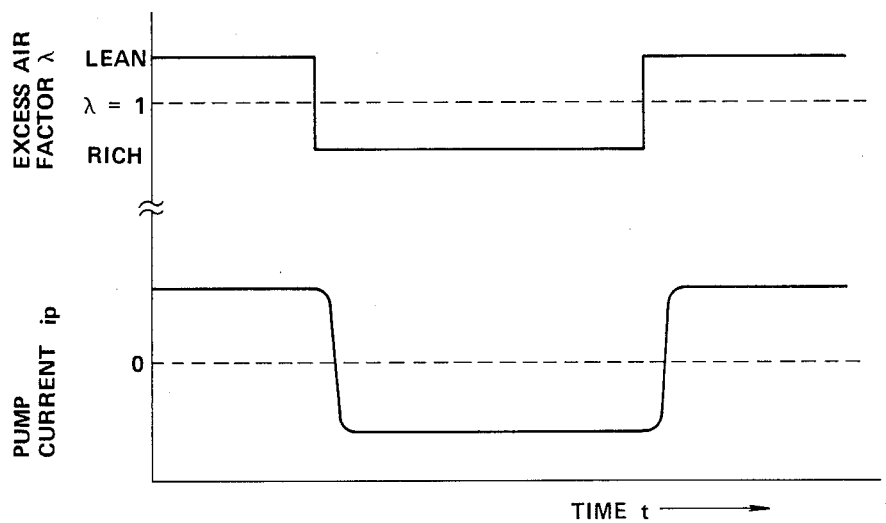
FIG. 4 is a graph showing an output characteristic of the air/fuel ratio sensor of FIG. 1A.
Figure 5:
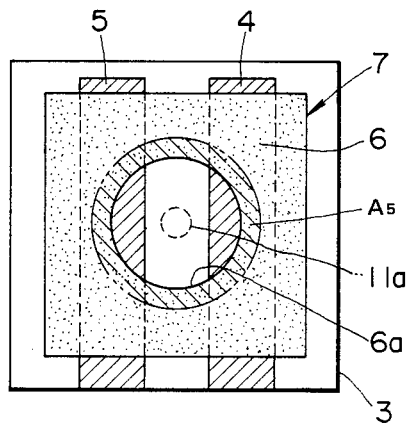
FIG. 5 is a plan view similar to FIG. 1B, showing a low resistivity region ($A_5$) of a metal oxide element of the air/fuel ratio sensor of FIG. 1A in a rich atmosphere.

FIG. 4 is a graph of an output characteristic of the air/fuel ratio sensor 1 according to the present invention. The characteristic of FIG. 4 is a response characteristic resulting from a change of the gas from lean to rich and vice versa. According to the present invention, the metal oxide primary element 6 is shaped and positioned so that the metal oxide does not exist inside the projection 11a of the hole 11. Especially in the rich atmosphere, the metal oxide element of the present invention 6 is held at a low resistivity state in a region $A_5$, which is not situated just below the gas diffusion hole 11, as shown in FIG. 5. Therefore, the oxygen concentration becomes excessively high only in a small part of the gas diffusion space 9, so that the gas in the diffusion space 9 can be renewed with a small amount of the pump current during a change between rich and lean. As a result, the air/fuel ratio sensor 1 of the present invention provides a satisfactory transient response characteristic having no overshoot, as shown in FIG. 4.

Figure 6A:
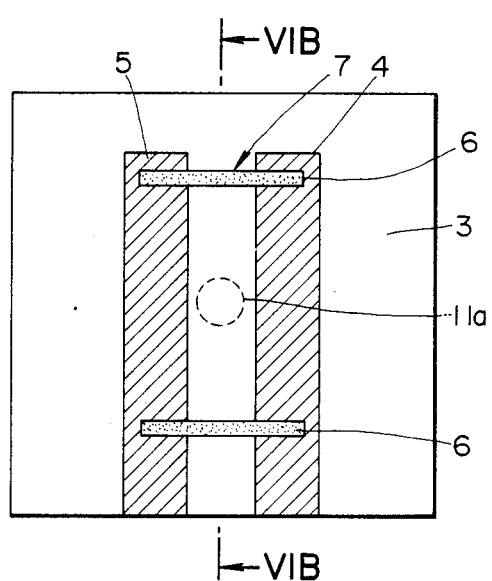
FIG. 6A is a plan view of an air/fuel ratio sensor of a second embodiment of the present invention, whose cover is removed.
Figure 6B:
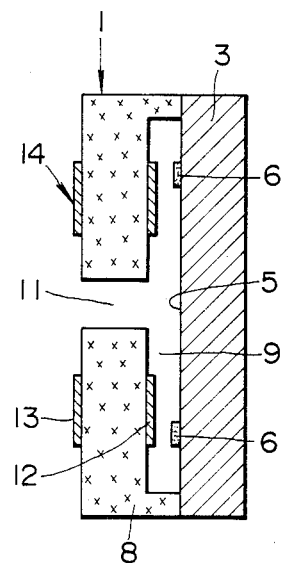
FIG. 6B is a sectional view taken on a line VIB—VIB of FIG. 6A, showing the air/fuel ratio sensor of the second embodiment including the cover.

A second embodiment of the present invention is shown in FIGS. 6A and 6B. In an air/fuel ratio sensor 1 of FIGS. 6A and 6B, the oxygen ion conductive solid electrolyte cover 8 is designed so that the rate of the gas diffusion is determined predominantly in the gas diffusion control space 9 instead of in the gas diffusion hole 11. For example, the diameter of the gas diffusion hole 11 is equal to 0.6 mm, and the height of the gas diffusion control space 9 (which is a distance between the inner surface of the top wall of the cover 8 and the upper surface of the substrate 3) is equal to 20 micrometers. In this embodiment, the surfaces of the first and second electrodes 4 and are flush with the surface of the substrate 5, and the metal oxide element 6 is divided in two pieces 6a and 6b, as shown in FIGS. 6A and 6B. Each piece of the metal oxide element 6 is shaped like a bar, and placed so that both ends are in contact with the first and second electrodes 4 and 5, respectively. Each piece of the metal oxide element 6 is spaced from the projection 11a of the hole 11 at a distance such that the rate of the gas diffusion is determined in a course between the position immediately below the gas diffusion hole 11 and the position of each piece 6a or 6b of the metal oxide element 6.

In the air/fuel ratio sensor of the second embodiment, the volume of the gas diffusion control space 9 is further reduced. That is, the amount of the gas to be replaced during a change between rich and lean is reduced. Therefore, the tendency to overshoot is further decreased, and the speed of response of the pump current ip is increased significantly (For example, the speed of response is more than five times as high as that of the conventional sensor).

Figure 20A:
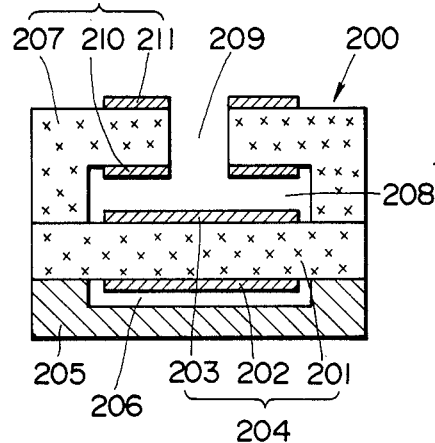
FIG. 20A is a vertical section of a conventional air/fuel ratio sensor of the same type as the sensors of the third and fourth embodiments of the present invention.
Figure 20B:
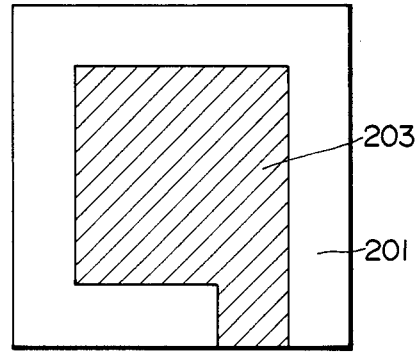
FIG. 20B is a plan view of the conventional sensor of FIG. 20A with its cover removed.

To facilitate understanding of third and fourth embodiments of the present invention, reference is made to a conventional air/fuel ratio sensor shown in FIG. 20A. (A similar sensor is disclosed in Japanese patent provisional publication No. 61-30758.)

An air/fuel ratio sensor 200 of FIG. 20A has a substrate 201 of an oxygen ion conductive solid electrolyte, which is sandwiched between first and second electrodes 202 and 203 to form an oxygen sensor cell 204. The first electrode 202 is enclosed by a lower cover 205 within a reference space 206 formed between the lower cover 205 and the substrate 201. A reference gas such as air is introduced into the reference space 206. The first electrode 202 in the reference space 206 serves as a reference electrode. The second electrode 203 is enclosed by an upper cover 207 of an oxygen ion conductive solid electrolyte, within a gas diffusion control space 208 formed between the solid electrolyte upper cover 207 and the solid electrolyte substrate 201. The upper cover 207 is formed with a small gas diffusion hole 209, through which a gas to be measured is introduced into the control space 208. Annular third and fourth electrodes 210 and 211 are attached to inner and outer surfaces of the upper cover 207 around the hole 209 to form an oxygen pump cell 212.

Figure 21:
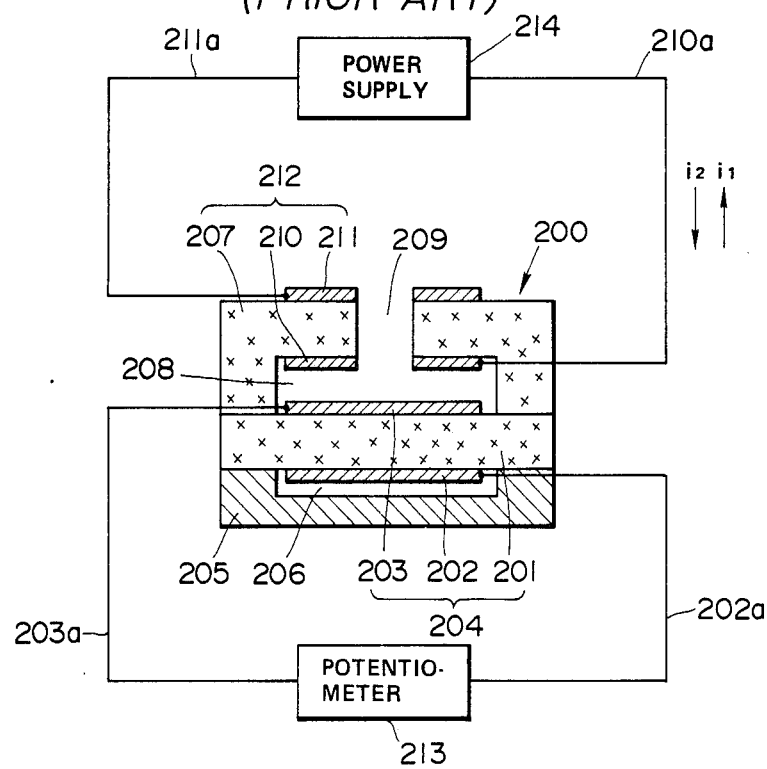
FIG. 21 is a circuit diagram showing a circuit using the conventional air/fuel ratio sensor of FIG. 20A.

As shown in FIG. 21, a potentiometer 213 is connected between the first and second electrodes 202 and 203 of the sensor cell 204 through leads 202a and 203a, and a power suply 214 is connected between the third and fourth electrodes 210 and 211 of the pump cell 212 through leads 210a and 211a.

Figure 22:
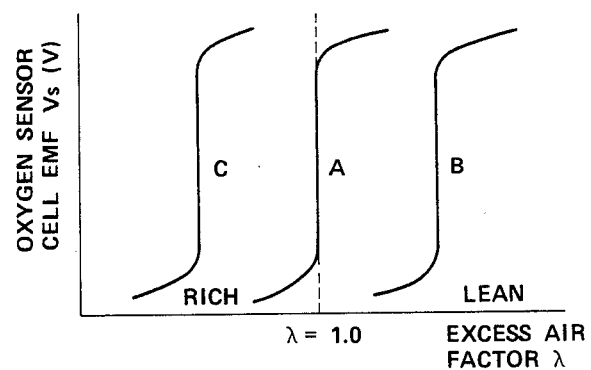
FIG. 22 is a graph showing oxygen sensor cell EMF versus excess air factor relationships of the conventional air/fuel ratio sensor of FIG. 20A.

When there is no pump current from the power supply 214, the difference in electric potential between the first and second electrodes 202 and 203 of the oxygen sensor cell 204, measured by the potentiometer 213 varies in dependence on the oxygen concentration of the gas introduced to the space 208 as shown by a characteristic A of FIG. 22. In this case, the potential difference, that is an oxygen sensor cell electromotive force, changes sharply at or near the A/F equivalent ratio (excess air factor) equal to 1. Like the sensor 101 shown in FIG. 7, the sensor 200 provides an oxygen sensor cell EMF versus excess air factor characteristic B of FIG. 22 when the pump current is supplied in the direction $i_1$ shown in FIG. 21, and a characteristic C of FIG. 22 when the pump current is supplied in the opposite direction $i_2$.

Figure 23:
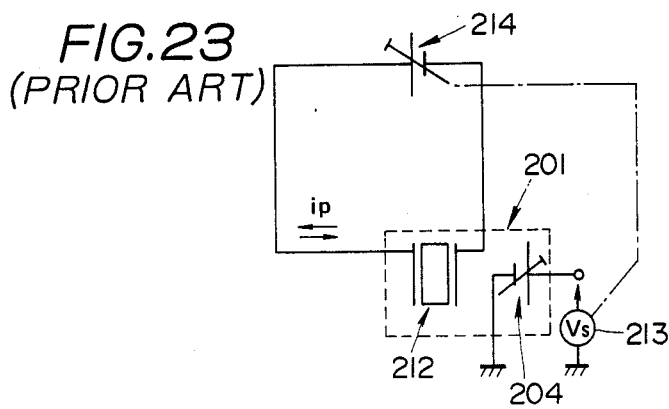
FIG. 23 is a diagram of an equivalent circuit arranged to measure the excess air factor by using the sensor of FIG. 20A.
Figure 24:
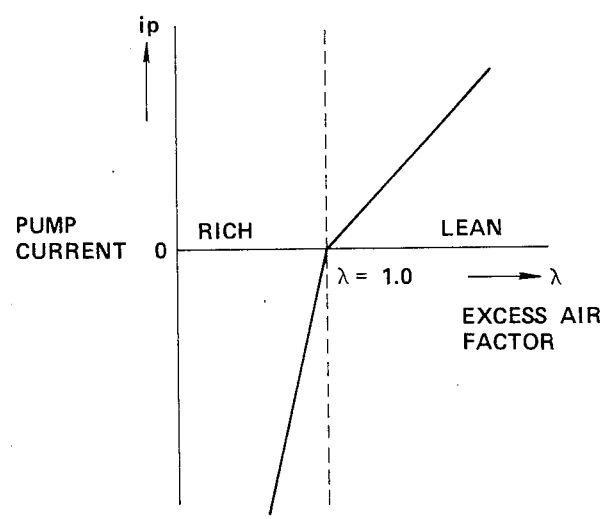
FIG. 24 is a graph showing a pump current versus excess air factor relationship of the equivalent circuit of FIG. 23, FIGS. 25A and 25B are schematic plan views of the conventional air/fuel ratio sensor of FIG. 20A, for showing high and low potential regions in lean and rich atmospheres.

An equivalent circuit shown in FIG. 23 is one example used in actual systems for measuring the excess air factor of exhaust gases. In the circuit of FIG. 23, the potentiometer 213 and the power supply 214 are connected to supply the pump current ip such that the electromotive force Vs of the oxygen sensor cell 104 is held at a predetermined value Va. FIG. 24 shows a characteristic of the pump current ip versus the excess air factor, obtained by the arrangement of FIG. 23.

Figure 25A:
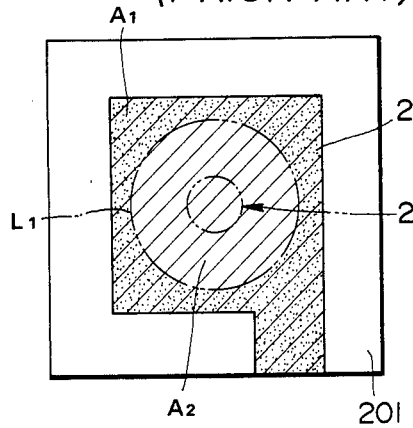
Figure 25B:
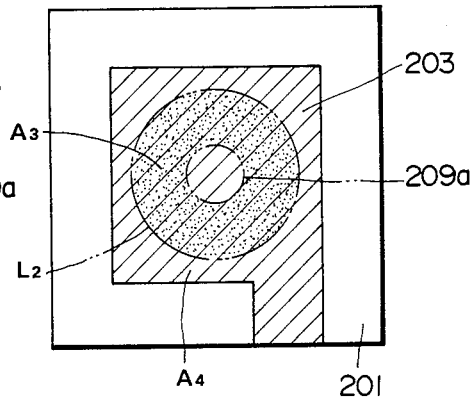

FIGS. 25A and 25B show the second electrode 203 of the sensor 200. When the gas to be measured is lean, the second electrode 203 is held at a high potential state with respect to the reference electrode in a region $A_1$ which is outside a two dot chain line circle $L_1$ and remote from a projection 209a of the hole 209, as shown in FIG. 25A. A region $A_2$ inside the circle $L_1$ is held at a low potential state. Therefore, a large part of the gas diffusion control space 208 must be held at a low oxygen concentration state by imposing an excessive load on the oxygen pump cell 212. When, on the other hand, the gas is rich, the second electrode 203 is held at the high potential state with respect to the reference electrode in a region $A_3$ lying near the projection 209a of the hole 209 inside a two dot chain line circle $L_2$ around the projection 209a, and at the low potential state in a remaining region $A_4$ outside the circle $L_2$, as shown in FIG. 25B. Therefore, a large part of the gas diffusion control space 208 must be held at a high oxygen concentration by imposing an excessive load on the oxygen pump cell 212. Because of the excessive load, the oxygen pump cell 212 of the conventional sensor 200 is subject to degradation in characteristic due to its use.

Figure 26:
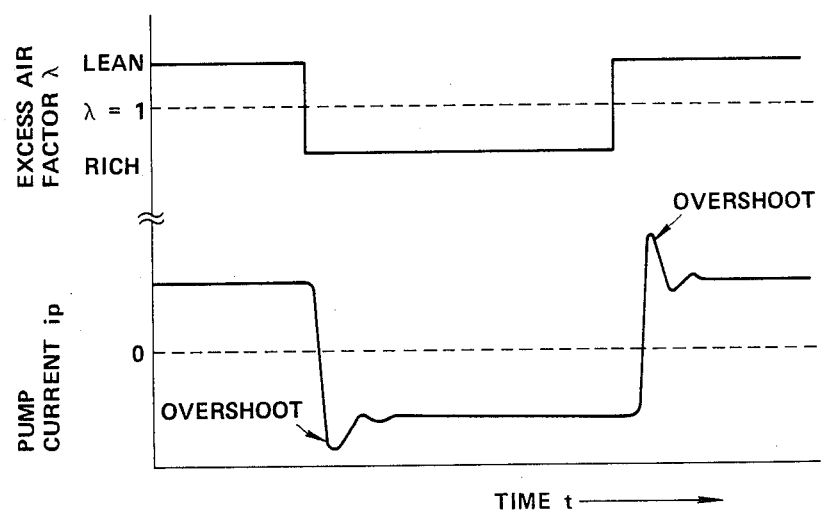
FIG. 26 is a graph showing a response characteristic of the sensor of FIG. 20A.

Furthermore, in changes in gas composition between rich and lean, the conventional sensor 200 requires a large amount of the pump current ip to remove an excess of oxygen due to a rich operation from the diffusion control space 208, and to supply a lack of oxygen due to a lean operation. Therefore, overshoots appear in a transient response characteristic of the pump current ip, as shown in FIG. 26.

The third embodiment of the present invention is shown in FIGS. 14A–18B.

Figure 14A:
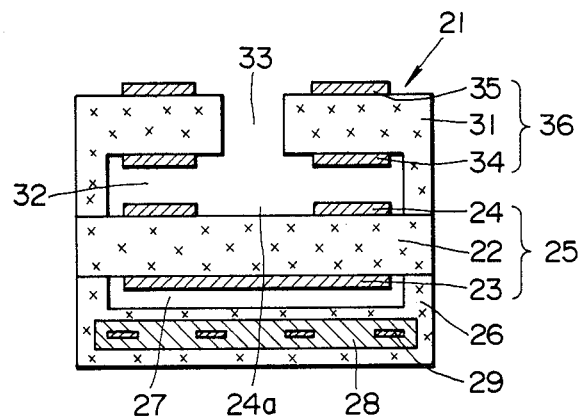
FIG. 14A is a vertical section schematically showing an air/fuel ratio sensor of a third embodiment of the present invention.

An air/fuel ratio sensor 21 shown in FIG. 14A has an oxygen ion conductive solid electrolyte substrate 22 of a plate shape, which is sandwiched between first and second electrodes 23 and 24 to form an oxygen sensor cell 25. The first electrode 23 is enclosed by a lower cover 26 within a reference gas space 27 formed between the lower cover 26 and the substrate 22. A reference gas such as air is introduced into the space 27, and the first electrode 23 is used as a reference electrode. The lower cover 26 has a heating element 29 which is electrically insulated by an insulator 28 and embedded in the cover 26.

Figure 14B:
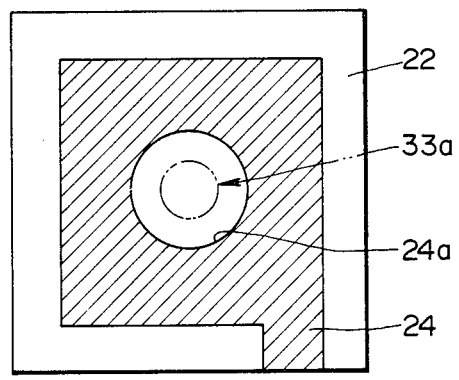
FIG. 14B is a plan view of the sensor of FIG. 14A in which a cover is removed.

The second electrode 24 is a primary measuring element in direct contact with the gas to be measured, and serves as a measuring electrode of the sensor cell 25. The second electrode 24 is formed with a circular opening 24a lying in a central part of the electrode 24. In this embodiment, the second electrode 24 is substantially square, and the center of the opening 24a coincides with the center of the second electrode 24, as shown in FIG. 14B. The second electrode 24 is enclosed by an upper cover 31 of an oxygen ion conductive solid electrolyte within a gas diffusion control space 32 formed between the upper cover 31 and the substrate 22. A circular gas diffusion hole 33 is formed in a central part of the upper cover 31. The upper cover 31 of this embodiment has a flat top wall which is substantially parallel to the substrate 22. The hole 33 of this embodiment is located at the center of the top wall of the upper cover 31, and extends through the top wall of the upper cover 31 in a direction substantially perpendicular to the top surface of the substrate 22. A two dot chain line small circle 33a of FIG. 14B is a projection produced by projecting the hole 33 onto the top surface of the substrate 22 in the direction in which the hole 33 extends through the upper cover 31. The circular opening 24a of the second electrode 24 is sized and located so that the circular opening 24a is substantially concentric with the circle 33a, and the diameter of the circular opening 24a is larger than that of the circle 33a. The second electrode 24 is shaped and located so that the second electrode 24 does not exist within the circle 33a.

Annular third and fourth electrodes 34 and 35 are attached, around the hole 33, to inner and outer surfaces of the top wall of the upper cover 31, respectively, to form an oxygen pump cell 36.

Figure 15:
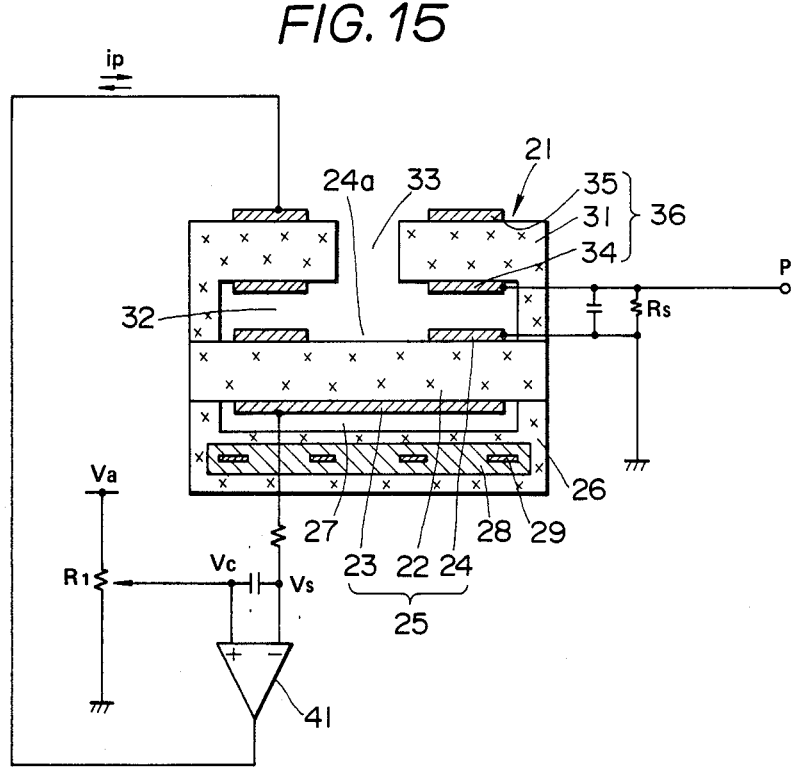
FIG. 15 is diagram of an air/fuel ratio detecting circuit using the sensor of FIG. 14A.

In a circuit of FIG. 15, an electromotive force Vs of the oxygen sensor cell 25 of the sensor 21 is inputted to a first input terminal (minus side) of a differential amplifier 41 whose second input terminal (plus side) is held at a reference voltage Vc. The differential amplifier 41 supplies the oxygen pump cell 36 with the pump current ip so that the electromotive force Vs of the sensor cell 25 is maintained equal to the reference voltage Vc.

Figure 16:
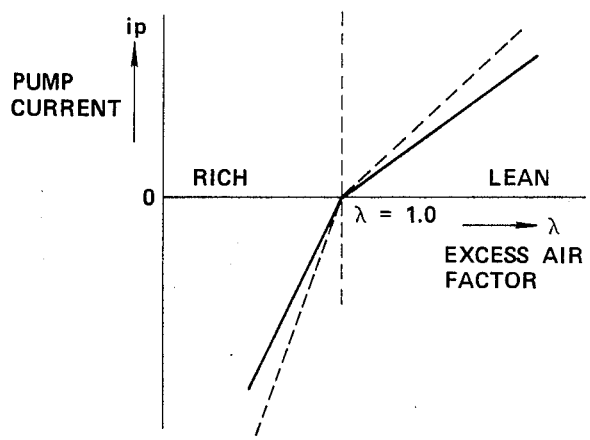
FIG. 16 is a graph showing a pump current versus excess air factor relationship of the air/fuel ratio sensor of FIG. 14A.

The air/fuel ratio sensor 21 of the third embodiment exhibits a pump curent versus excess air factor characteristic shown by a solid line in FIG. 16. A broken line in FIG. 16 shows a characteristic of the conventional sensor 200 of FIG. 20A. In the sensor of the third embodiment, the absolute value of the pump curent is reduced on both of the rich and lean sides, as compared with the conventional sensor 200. Thus, the load on the pump cell 36 is reduced, and the undesired aging of the sensor output characteristic is limited.

Figure 17:
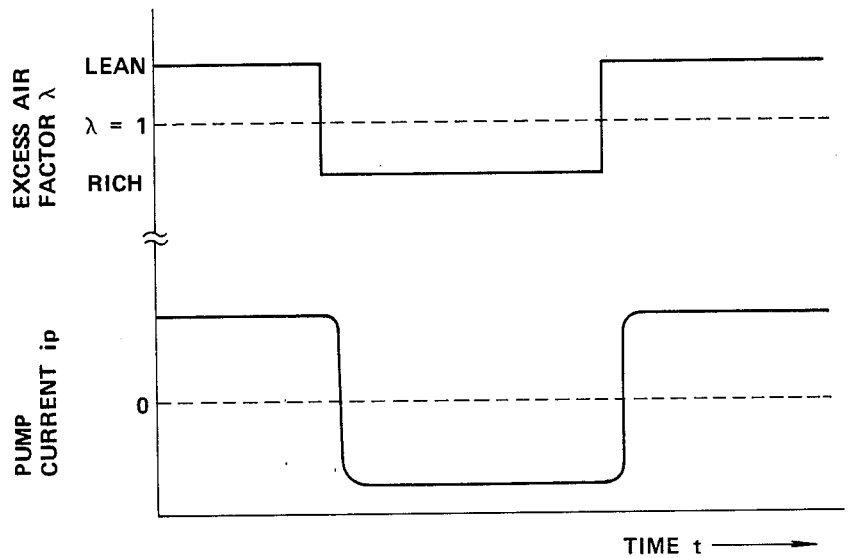
FIG. 17 is a graph showing a response characteristic of the air/fuel ratio sensor of FIG. 14A, FIGS. 18A and 18B are plan views similar to FIG. 14B, for showing high potential region and low potential region.
Figure 18A:
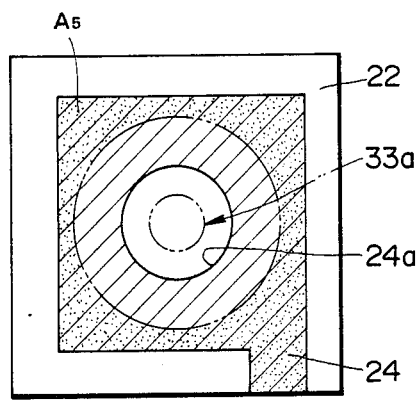
Figure 18B:
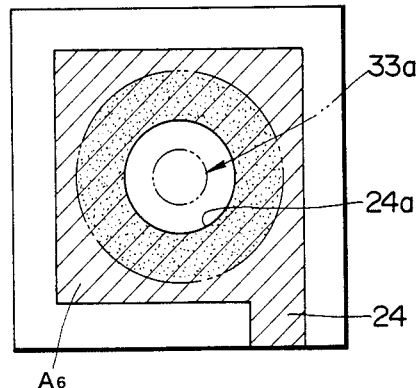

The air/fuel ratio sensor 21 exhibits a satisfactory transient response characteristic having no overshoot, as shown in FIG. 17. The second electrode 24 is held at a high potential state in a region $A_5$ shown in FIG. 18A in the case of a lean atmosphere, and at a low potential state in a region $A_6$ shown in FIG. 18B in the case of a rich atmosphere. Each of the regions $A_5$ of FIG. 18A and the region $A_6$ of FIG. 18B is situated apart from the position right below the gas diffusion hole 33a, so that the oxygen concentration is held at an excessively high or excessively low value only in a small volume of the gas diffusion space 32. Therefore, the gas in the control space 32 can be easily renewed with a small amount of the pump current, and overshoot is prevented as shown in FIG. 17.

Figure 19A:
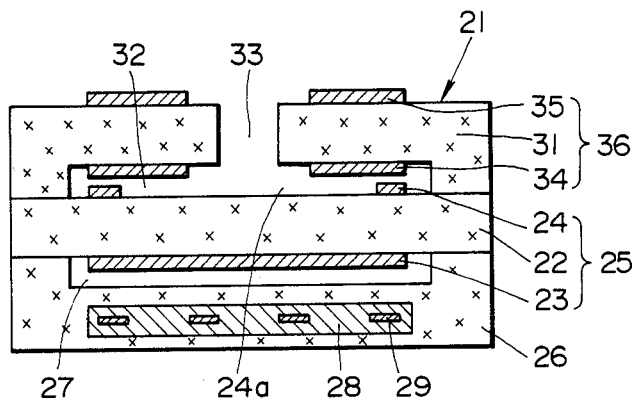
FIG. 19A is a vertical section schematically showing an air/fuel ratio sensor of a fourth embodiment of the present invention.
Figure 19B:
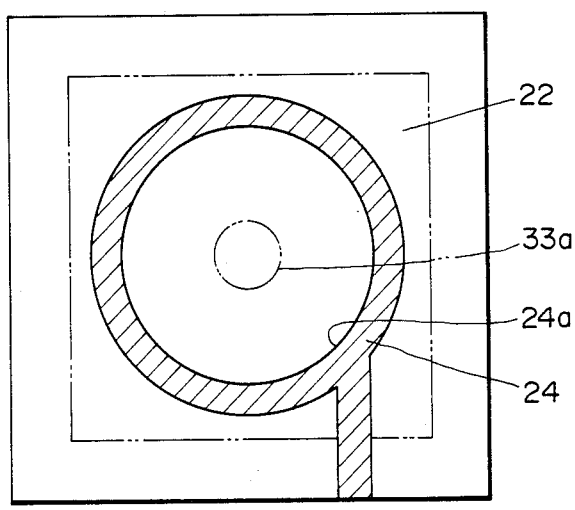
FIG. 19B is a plan view of the air/fuel ratio sensor of FIG. 19A in which a cover is removed.

A fourth embodiment of the present invention is shown in FIGS. 19A and 19B. An air/fuel ratio sensor 21 of the fourth embodiment is basically identical to the sensor of the third embodiment. As in the second embodiment, the upper cover 31 of the fourth embodiment is designed so that the rate of the gas diffusion is determined predominantly in the gas diffusion control space 32 instead of in the gas diffusion hole 33. For example, the diameter of the gas diffusion hole 33 is equal to 0.6 mm, and the height of the control space 32 (which is a distance between the substrate 22 and the top wall of the upper cover 31) is equal to 20 micrometers. The second electrode 24 of the fourth embodiment is narrow, and shaped like a ring as shown in FIG. 19B. The ring-shaped second electrode 24 is placed around the projection 33a of the hole 33. In the fourth embodiment, the second electrode 24 is situated at a considerable distance from the projection 33a, and the rate of the gas diffusion is determined in the interval between the point immediately below the hole 33 and the second electrode 24.

Like the second embodiment, the sensor of the fourth embodiment can further reduce the tendency to overshoot, and increase the speed of response approximately to a value five times as high as that of the conventional example.

There are known in the art various oxygen conductive solid electrolytes usable in the present invention, various metal oxides usable as the metal oxide element 6 of the first and second embodiments, and various materials usable as the electrodes of the sensor cell and the pump cell of the present invention.

What is claimed is:

1. An air/fuel ratio sensing device comprising;
   sensing means comprising a substrate and a primary measuring element mounted on a first surface of said substrate, and
   controlling means comprising a first cover mounted on said substrate for enclosing said primary element within a control space formed between said substrate and said first cover, said first cover being formed with a hole for allowing a gas to move into and out of said control space, said control space and said hole being shaped and sized so that a rate of gas diffusion is determined substantially in said hole rather than said control space, at least a part of said first cover being made of an oxygen ion conductive solid electrolyte, said controlling means further comprising inner and outer electrodes forming an oxygen pump cell with said oxygen ion conductive solid electrolyte, said inner electrode being attached to an inner surface of said first cover inside said control space, and said outer electrode being attached to an outer surface of said first cover outside said control space, said primary element of said sensing means being disposed outside a projection of said hole formed by projecting said hole onto said first surface of said substrate along a line along which said hole extends.

2. A device according to claim 1 wherein said primary element is shaped and positioned so that said primary element is not situated inside a circle which lies in said first surface of said substrate, and has a center just below said hole and an area greater than a cross sectional area of said hole.

3. A device according to claim 2 wherein said first surface of said substrate is substantially flat, and said hole extends through said first cover along a line substantially perpendicular to said first surface of said substrate.

4. A device according to claim 3 wherein said first cover has a top wall substantially flat and parallel to said first surface of said substrate, said hole being formed in said top wall, each of said inner and outer electrodes being annular and disposed on said top wall around said hole.

5. A device according to claim 4 wherein said hole is circular, and said primary element has a circular opening whose center lies on an axis of said hole and whose diameter is greater than a diameter of said hole.

6. A device according to claim 2 wherein said primary measuring element is made of a metal oxide whose electrical resistance is variable in dependence on an oxygen concentration of a gas in contact therewith, and said sensing means further comprises first and second electrodes attached to said primary element to measure the electrical resistance of said primary element.

7. A device according to claim 6 further comprising external circuit means coupled to said first, second, inner and outer electrodes for supplying said oxygen pump cell with an electrical current of such a magnitude as to maintain an electrical output of said sensing means at a constant value.

8. A device according to claim 2 wherein said substrate is at least partly made of an oxygen ion conductive solid electrolyte, and said sensing means comprises a reference electrode attached to said substrate to form an oxygen sensor cell together with said primary element serving as a measuring electrode and said oxygen ion conductive solid electrolyte of said substrate.

9. A device according to claim 8 wherein said reference electrode of said oxygen sensor cell is attached to a second surface of said substrate, and enclosed by a second cover within a reference gas space.

10. A device according to claim 9 wherein said primary element has a circular opening whose center lies just below said hole, and whose area is greater than a cross sectional area of said hole.

11. A device according to claim 10 wherein said primary element is shaped like a ring.

12. A device according to claim 11 wherein said control space and said hole are shaped and sized so that a rate of gas diffusion is determined in said control space rather than said hole.

13. A device according to claim 8 further comprising external circuit means coupled to said inner, outer, measuring and reference electrodes of said oxygen pump cell and said oxygen sensor cell for supplying said oxygen pump cell with an electrical pump current of such a magnitude as to maintain an electrical output of said oxygen sensor cell at a constant value.

14. An air/fuel ratio sensing device comprising;
sensing means comprising a substrate and a primary measuring element mounted on a first surface of said substrate, and
controlling means comprising a first cover mounted on said substrate for enclosing said primary element within a control space formed between said substrate and said first cover, said first cover being formed with a hole for allowing a gas to move into and out of said control space, at least a part of said first cover being made of an oxygen ion conductive solid electrolyte, said controlling means further comprising inner and outer electrodes forming an oxygen pump cell with said oxygen ion conductive solid electrolyte, said inner electrode being attached to an inner surface of said first cover inside said control space, and said outer electrode being attached to an outer surface of said first cover outside said control space, said primary element of said sensing means being disposed outside a projection of said hole formed by projecting said hole onto said first surface of said substrate along a line along which said hole extends, wherein said primary element has a circular opening whose center lies just below said hole and whose area is greater than a cross-sectional area of said hole.

15. An air/fuel ratio sensing device comprising;
sensing means comprising a substrate and a primary measuring element mounted on a first surface of said substrate, and
controlling means comprising a first cover mounted on said substrate for enclosing said primary element within a control space formed between said substrate and said first cover, said first cover being formed with a hole for allowing a gas to move into and out of said control space, at least a part of said first cover being made of an oxygen ion conductive solid electrolyte, said controlling means further comprising inner and outer electrodes forming an oxygen pump cell with said oxygen ion conductive solid electrolyte, said inner electrode being attached to an inner surface of said first cover inside said control space, and said outer electrode being attached to an outer surface of said first cover outside said control space, said primary element of said sensing means being disposed outside a projection of said hole formed by projecting said hole onto said first surface of said substrate along a line along which said hole extends, wherein said primary element comprises first and second pieces placed on said first surface of said substrate apart from a position just below said hole.

16. A device according to claim 15 wherein said control space and said hole are shaped and sized so that a rate of gas diffusion is determined in said control space rather than said hole.

* * * * *